US008648169B2

(12) United States Patent
Saragovi

(10) Patent No.: US 8,648,169 B2
(45) Date of Patent: Feb. 11, 2014

(54) METHODS OF USE OF TRK RECEPTOR MODULATORS

(75) Inventor: H. Uri Saragovi, Montreal (CA)

(73) Assignee: The Royal Institution for the Advancement of Learning/McGill University (CA)

( * ) Notice: Subject to any disclaimer, the term of this patent is extended or adjusted under 35 U.S.C. 154(b) by 771 days.

(21) Appl. No.: 12/312,975

(22) PCT Filed: Dec. 5, 2007

(86) PCT No.: PCT/US2007/024936
§ 371 (c)(1),
(2), (4) Date: Jun. 24, 2009

(87) PCT Pub. No.: WO2008/070132
PCT Pub. Date: Jun. 12, 2008

(65) Prior Publication Data
US 2010/0048461 A1 Feb. 25, 2010

Related U.S. Application Data

(60) Provisional application No. 60/873,042, filed on Dec. 5, 2006.

(51) Int. Cl.
*A61K 38/00* (2006.01)
(52) U.S. Cl.
USPC ............ 530/317; 530/323; 514/2.9; 514/913
(58) Field of Classification Search
None
See application file for complete search history.

(56) References Cited

U.S. PATENT DOCUMENTS

| 4,911,920 A | 3/1990 | Jani et al. |
| 6,881,719 B2 | 4/2005 | Saragovi et al. |
| 2002/0194630 A1 | 12/2002 | Manning, Jr. et al. |
| 2009/0318335 A1 | 12/2009 | Vitagliano et al. |

FOREIGN PATENT DOCUMENTS

| EP | 0 525 475 A2 | 2/1993 |
| WO | WO 93/23082 A1 | 11/1993 |
| WO | WO 95/20378 A1 | 8/1995 |
| WO | WO 01/52843 A1 | 7/2001 |
| WO | WO 0152843 A1 * | 7/2001 |
| WO | WO 2007/062101 A2 | 5/2007 |
| WO | 2008056217 A1 | 5/2008 |
| WO | WO 2008/070132 A2 | 6/2008 |

OTHER PUBLICATIONS

Osborne et. al. Topically Applied Betaxolol Attenuates NMDA-induced Toxicity to Ganglion Cells and the Effects of Ischemia to the Retina. Exp. Eye Res. vol. 69, 331-342 (1999).*
Middendorf et. al. Predicting Genetic Regulatory Response Using Classification. Bioinformatics. vol. 00, No. 00, p. 1-8 (2004).*
Malhis, N., and Ruttan, A., Detecting Gene Regulation Relations from Microarray Time Series Data, Proceedings of the 2006 International Conference on Machine Learning; Models, Technologies & Applications MLMTA'06, Jun. 2006, Las Vegas, Nevada, USA.*
Zou and Conzen. A new dynamic Bayesian network (DBN) approach for identifying gene regulatory networks from time course microarray data. Bioinformatics. vol. 21, Issue 1. p. 71-79 (2005).*
Osborne et. al. (Topically Applied Betaxolol Attenuates NMDA-induced Toxicity to Ganglion Cells and the effects of Ischemia to the Retina, Exp. Eye Res. (69) 331-342, 1999).*
Hapner, S.J., et al., "Neural Differentiation Promoted by Truncated trkC Receptors in Collaboration with p75$^{NTR}$," *Dev. Biol.*, 201:90-100 (1998).
Khursigara, G., et al., "Association of the p75 Neurotrophin Receptor with TRAF6," *J Biol. Chem.*, 274(5):2597-2600 (1999).
LeSauteur, L., et al., "Potent Human p140-TrkA Agonists Derived from an Anti-Receptor Monoclonal Antibody," *J. Neurosci.*, 16(4):1308-1316 (1996).
LeSauteur, L., et al., "Small Peptide Mimics of Nerve Growth Factor Bind TrkA Receptors and Affect Biological Responses," *J. Bio. Chem.*, 270(12): 6564-6569 (1995).
Maliartchouk, S., et al., "A Designed Peptidomirnetic Agonistic Ligand of TrkA Nerve Growth Factor Receptors," *Mol. Pharm.*, 57:385-391 (2007).
Palko, M.E., et al., "Evidence for a Role of Truncated trkC Receptor Isoforms in Mouse Development," *J. Neurosci.*, 19(2):775-782 (1999).
Pattarawarapan, M., et al., "New Templates for Syntheses of Ring-Fused, $C^{10}$ β-Turn Peptidomimetics Leading to the First Reported Small-Molecule Mimic of Neurotrophin-3," *J. Med. Chem.*, 45(20):4387-4390 (2002).
Rudzinski, M., et al., "Changes in Retinal Expression of Neurotrophins and Neurotrophin Receptors Induced by Ocular Hypertension," *J. Neurobiol*, 58:341-354 (2004).
Saragovi, H.U., et al., "A TrkA-Selective, Fast Internalizing Nerve Growth Factor-Antibody Complex Induces Trophic but not Neuritogenic Signals," *J. Biol. Chem.* 273(52):34933-34940 (1998).
Tsai, J.C., et al., "Current and Emerging Medical Therapies for Glaucoma," *Expert Opin. Emerging Drugs*, 10(1):109-118 (2005).
Tsoulfas, P., et al., "The Rat *trkC* Locus Encodes Multiple Neurogenic Receptors that Exhibit Differential Response to Neurotrophin-3 in PC12 Cells," *Neuron*, 10(5):975-990 (1993).
Valenzuela, D.M., et al., "Alternative Forms of Rat TrkC with Different Functional Capabilities," *Neuron*, 10(5):963-974 (1993).

(Continued)

*Primary Examiner* — Cecilia J Tsang
*Assistant Examiner* — Jeanette Lieb
(74) *Attorney, Agent, or Firm* — Pillsbury Winthrop Shaw Pittman LLP

(57) ABSTRACT

The present invention relates to methods of treating or preventing retinal ganglion cell (RGC) death and/or glaucoma using modulators of neurotrophic receptors that comprise β-turn peptidomimetic cyclic compounds or derivatives thereof. The neurotrophic receptor modulators can be used alone, in combination and/or in conjunction with one or more other compounds, molecules or drugs that treat or prevent ocular hypertension, RGC death and/or glaucoma.

2 Claims, 5 Drawing Sheets

(56) References Cited

OTHER PUBLICATIONS

Zaccaro, M.C., el al., "Selective Small Molecule Peptidomimetic Ligands of TrkC and TrkA Receptors Afford Discrete or Complete Neurotrophic Activities," *Chem. Biol.*, 12:1015-1028 (2005).

Notification of Transmittal of the International Search Report and the Written Opinion of the International Searching Authority, or the Declaration, from International Application No. PCT/US2007/024936, mailed Nov. 11, 2008.

Notification Concerning Transmittal of International Preliminary Report on Patentability, from International Application No. PCT/US2007/024936, mailed Jun. 18, 2009.

Feng, Y. and Burgess, K., "Solid-Phase $S_NAr$ Macrocyclizations to Given Turn—Extended-turn Peptidomimetics," *Chem. Eur. J.*, 5(11):3261-3272 (1999).

Feng, Y., et al., "Stereochemical Implications on Diversity in β-Turn Peptidomimetic Libraries," *J. Org. Chem.*, 64:9175-9177 (1999).

Nguyen, D.H., et al., "Growth Factor and Neurotrophic Factor mRNA in Human Lacrimal Gland," *Cornea*, 16(2):192-199 (1997).

Saragovi, H.U. and Burgess, K., "Small Molecule and Protein-Based Neurotrophic Ligands: Agonists and Antagonists as Therapeutic Agents," *Exp. Opin. Ther. Patents*, 9(6):737-751 (1999).

Wang, Z., "Conformations of Peptidomimetics Formed by SNAr Macrocyclizations: 13- to 16-Membered Ring Systems," *Chem. Eur. J.*, 5(11):3273-3278 (1999).

Colangelo, A.M., A New Nerve Growth Factor-Mimetic Peptide Active on Neuropathic Pain in Rats, 2008, J. of Neuroscience, 28(11)2698-2709.

\* cited by examiner

FIG 1A.
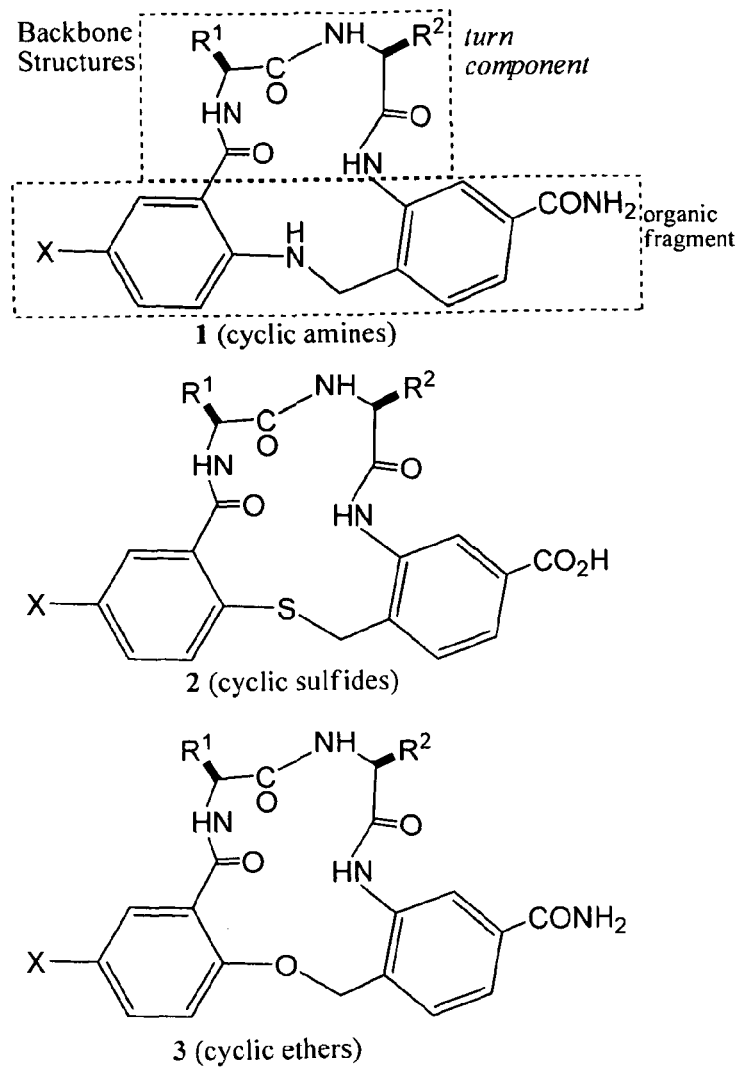
FIG 1B.
X-Substituents
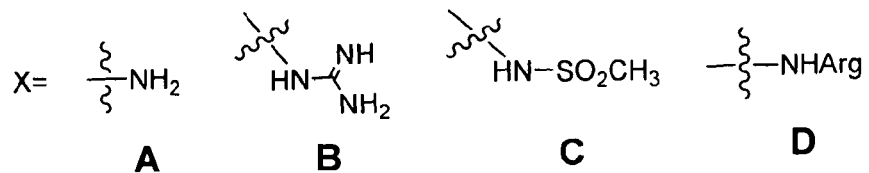
FIG 1C.
Dipeptide Fragments
| IK | NN | GK | EK | IR | TG |
|----|----|----|----|----|-----|
| a  | b  | c  | d  | e  | f  |
| KG | IN | KT | EN | RG |
|----|----|----|----|-----|
| g  | h  | i  | j  | k  |

D.

| Code | aa | Scaffold | X |
|---|---|---|---|
| 1Aa | IK | amine | amine |
| 1Ad | EK | amine | amine |
| 1Ba | IK | amine | guanidine |
| 3Aa | IK | ether | amine |
| 3Ac | GK | ether | amine |
| 3Ae | IR | ether | amine |
| 3Ak | RG | ether | amine |
| 3Ba | IK | ether | guanidine |
| 3Bg | KG | ether | guanidine |
| 3Bi | KT | ether | guanidine |
| 3Ca | IK | ether | MeSO$_2$NH |
| 3Ce | IR | ether | MeSO$_2$NH |
| 3Cg | KG | ether | MeSO$_2$NH |
| 3Ck | RG | ether | MeSO$_2$NH |

TrkC receptor agonists

FIG. 1D

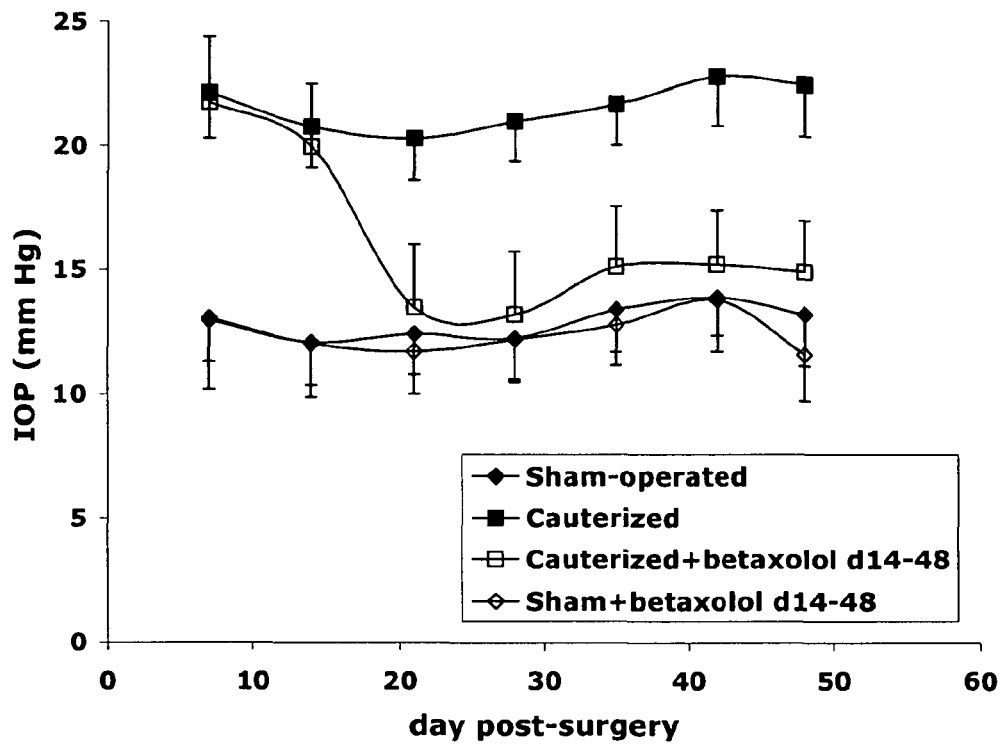

Pharmacological reduction of high IOP. Mean IOP values ± sd, n=6. At day 0, eyes were surgically cauterized to increase IOP, or were sham-cauterized with normal IOP. From day 14 onwards the indicated groups were treated daily with β-blocker (betaxolol 0.5%, Alcon Labs); the other groups were untreated. Daily treatment with β-blocker continued until day 48, and the animals were sacrificed on day 49 to collect their retinas.

FIG. 2

| | O.D. | O.S. | | O.D. | O.S. |
|---|---|---|---|---|---|
| Day 0 | Sham operated | Cauterized | | Sham operated | Cauterized |
| | Normal IOP | High IOP | ↓ | Normal IOP | High IOP |
| | 14 days to allow disease progression and some RGC death in high IOP eyes ||||||
| | ↓ | ↓ | | ↓ | ↓ |
| 14 thru 42 | | | | Betaxolol daily (until end date day 42 or 49) | Betaxolol daily (until end date day 42 or 49) |
| | | | ↓ | | |
| | Normal IOP | High IOP | | Normal IOP | Normalized IOP |
| | | | ↓ | | |
| 14 and 21 | PHARMACOLOGICAL TREATMENTS at days 14 and 21 (intraocular injections of D3, C(28-35), vehicle, or controls) |||||
| | | | ↓ | | |
| 33 | RETROGRADE LABELING |||||
| | | | ↓ | | |
| 42 or 49 | SACRIFICE, PROCESS RETINAS, COUNT RGCs |||||

Experimental Flowchart. OD = right eye, OS = left eye.

FIG. 3

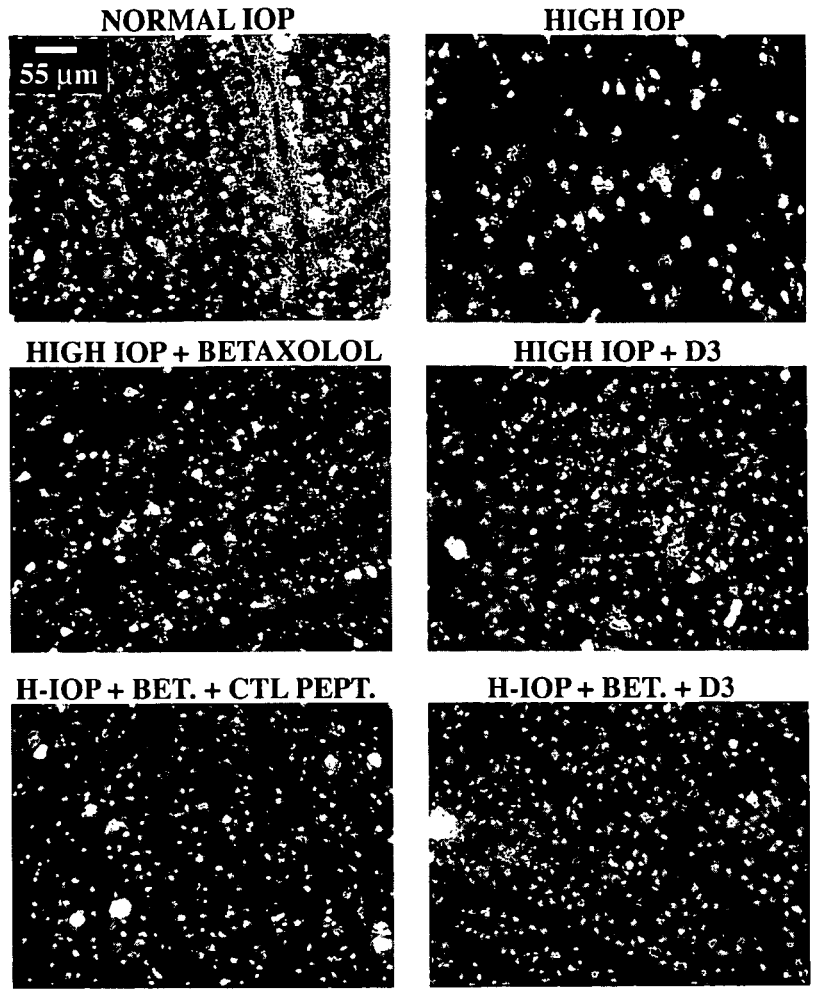

Representative micrographs of retinas. Retrogradely labeled retinas were collected and flat mounted. Pictures show RGC labeled from normal retinas (normal IOP), day 42 high IOP retinas, day 42 high IOP retinas treated with betaxolol from day 14 onwards, day 42 high IOP retinas treated with D3 at days 14 and 21, day 42 high IOP retinas treated with combination betaxolol + control peptidomimetic, or day 42 high IOP retinas treated with combination betaxolol + D3.

FIG. 4

METHODS OF USE OF TRK RECEPTOR MODULATORS

RELATED APPLICATIONS

This application is the U.S. National Stage of International Application No. PCT/US2007/024936, filed Dec. 5, 2007, published in English, and claims the benefit of U.S. Application No. 60/873,042, filed Dec. 5, 2006. The entire teachings of the above application applications are incorporated herein by reference.

GOVERNMENT SUPPORT

The invention was supported, in part, by grant CA82642, NS38569 and CA74289 from the National Institute of Health and, in part, by grants MTI3265, MOP57690 and CI-CFA-41478 from the Canadian Institutes of Health Research. The Government has certain rights in the invention.

BACKGROUND OF THE INVENTION

Vision impairment due to glaucoma affects millions of people worldwide with hundreds of thousands of new cases of glaucoma diagnosed in the United States each year. In open angle glaucoma, the most frequent form of the disease, visual field loss is caused by progressive optic nerve fiber loss concomitant with elevated intraocular pressure (IOP). High IOP due to aqueous humor buildup is a major risk factor of glaucoma, and is thought to induce chronic and progressive death of retinal ganglion cells (RGCs). It is estimated that RGCs die by apoptosis at a constant rate of approximately 4% per week during continuous exposure to ocular hypertension, leading to nerve damage. Although treatments are often successful at normalizing high IOP, progressive RGC death and visual field loss generally continue.

Lack of trophic support by a family of growth factors known as neurotrophins (NTFs) has been suggested as a factor in RGC death in glaucoma. NTFs regulate neuronal development, growth, survival, differentiation, maintenance of neuronal cell phenotype and function. The NTFs include Nerve Growth Factor (NGF), Brain Derived Neurotrophic Factor (BDNF), Neurotrophin-3 (NT-3) and Neurotrophin-4 (NT-4) and these NTFs bind to two transmembrane receptors, the high affinity receptor family tyrosine kinase (Trk) (TrkA, Trk B and Trk C) ($K_d$=10-100 pM) and the p75 receptor ($K_d$=1 nM). Although Trk family receptor ligands are quite selective (e.g., NGF binds TrkA, BDNF binds TrkB; and NT-3 binds mainly TrkC), the p75 receptor is bound non-selectively by all NTFs, making its activation quite promiscuous. The two receptors are believed to have opposing actions, with Trk family receptors mediating signal transduction associated with "positive" signals of cell survival and differentiation, maintenance and repair. The p75 receptor is thought to regulate ligand affinity for Trk receptors and, consequently, ligand-dependent Trk activation and concomitant tyrosine kinase activity, in addition to its own pro-apoptotic activity in some cell types, including retinal neurons.

Still, the use of receptor ligands believed to be involved in RGC apoptosis in glaucoma as therapeutics appears to be limited. The complex and often opposite functions associated with ligand binding to Trk and p75 receptors and the activation of multiple and pleiotrophic pathways makes in vivo NTF pharmacology difficult to predict. Indeed, clinical trials using recombinant NTF polypeptides to treat glaucoma have generally been disappointing. Further, recombinant proteins (e.g., NGF and other receptor ligands) for use in medical treatments tend to be difficult to manufacture and expensive to produce. What is needed is a treatment for glaucoma that halts RGC apoptosis and thus, disease progression due to continued vision (field) loss. A treatment that, unlike intraocular pressure normalizing drugs alone, targets the molecular mechanism underlying the death of RGCs and one that is specific enough to be effective.

SUMMARY OF THE INVENTION

The present invention relates to methods of treating or preventing retinal ganglion cell (RGC) death, in particular, RGC death associated with glaucoma, using compounds and/or peptides that modulate the activity of neurotrophin receptors. Specifically, in one embodiment, the invention relates to a method of treating or preventing RGC death or glaucoma in a subject by administering an effective amount of a composition comprising a selective TrkA receptor agonist and a suitable pharmaceutical carrier and at least one intraocular pressure-normalizing drug. In one embodiment, the TrkA receptor agonist comprises a β-turn peptidomimetic cyclic compound having a macrocyclic ring of 13 to 17 carbon atoms. In a further embodiment, the β-turn peptidomimetic cyclic compound has the formula (I):

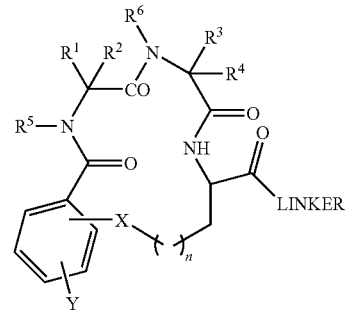

wherein $R^1$ and $R^3$ are selected from hydrogen, $C_1$ to $C_6$ alkyl or aryl substituents found in a natural or unnatural amino acid; $R^2$ and $R^4$ are hydrogen or $C_1$ to $C_6$ alkyl; $R^5$ and R are hydrogen; $R^1$ and $R^2$ or $R^3$ and $R^4$ together with the carbon atom to which they are attached form a cyclopropyl, cyclobutyl, cyclopentyl or cyclohexyl group; Y is hydrogen or one or two aromatic substituents; X is selected from O, N, S, P, Se, C, alkylene of 1 to 6 carbon atoms, SO, $SO^2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$ and CHO. Another suitable LINKER group is NH—$CH_2$—COOH.

In another embodiment of the present invention X is O, S or NH, $R^1$, $R^3$, $R^5$ and $R^6$ are each hydrogen atoms and the macrocyclic ring has 14, 15 or 16 ring atoms.

In another embodiment, $R^1$ and $R^3$ are derived from a sequence of different amino acids side chains selected from natural and synthetic amino acids.

In another embodiment of the present invention, X is —O—, —S— or —NH—.

In a particular embodiment, the β-turn peptidomimetic cyclic compound has the formula:

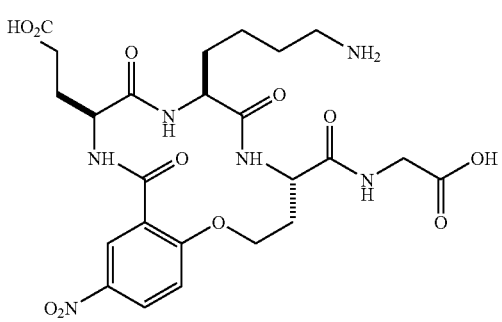

The intraocular pressure-normalizing drug can be one selected from the group consisting of parasympathomimetic agents, cholinergic agents, sympathomimetic agents, sympatholytic agents, carbonic anhydrase inhibitors, prostaglandin analogs, docosanoids and osmotic agents.

In yet another embodiment, the method further comprises administering an effective amount of a composition comprising an antagonist of the p75 receptor or, in another embodiment, a composition that regulates the expression or activity of one or more intraocular pressure-regulated early genes (IPREGs).

The present invention also relates to a method of treating or preventing RGC death or glaucoma in a subject by administering to the subject an effective amount of a composition comprising a selective TrkA receptor agonist comprising a β-turn peptidomimetic cyclic compound having a macrocyclic ring of 13 to 17 carbon atoms and a suitable pharmaceutical carrier. In a particular embodiment, this β-turn peptidomimetic cyclic compound has the formula of:

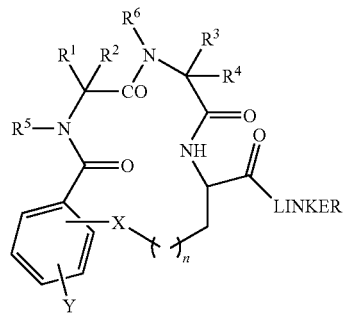

wherein $R^1$ and $R^3$ are selected from hydrogen, $C_1$ to $C_6$ alkyl or aryl substituents found in a natural or unnatural amino acid; $R^2$ and $R^4$ are hydrogen or $C_1$ to $C_6$ alkyl; $R^5$ and $R^6$ are hydrogen; $R^1$ and $R^2$ or $R^3$ and $R^4$ together with the carbon atom to which they are attached form a cyclopropyl, cyclobutyl, cyclopentyl or cyclohexyl group; Y is hydrogen or one or two aromatic substituents; X is selected from O, N, S, P, Se, C, alkylene of 1 to 6 carbon atoms, SO, $SO^2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$ and CHO. Another suitable LINKER group is $NH-CH_2-COOH$. Most particularly, the compound is D3 having the formula:

In one embodiment, the method can further comprise administering an intraocular pressure-normalizing drug. In another embodiment, the method further comprises administering an effective amount of a composition comprising a p75 receptor antagonist or one that regulates the expression or activity of one or more IPREGs.

A method is also provided for the treatment of RGC death or glaucoma in a subject, the method comprising administering to the subject and effective amount a composition comprising a Trk C receptor agonist and a suitable pharmaceutical carrier. In one embodiment, an intraocular pressure normalizing drug is also administered with the TrkC receptor agonist. In yet another embodiment, the TrkC receptor agonist is also a β-turn cyclic compound selected from the group consisting of:

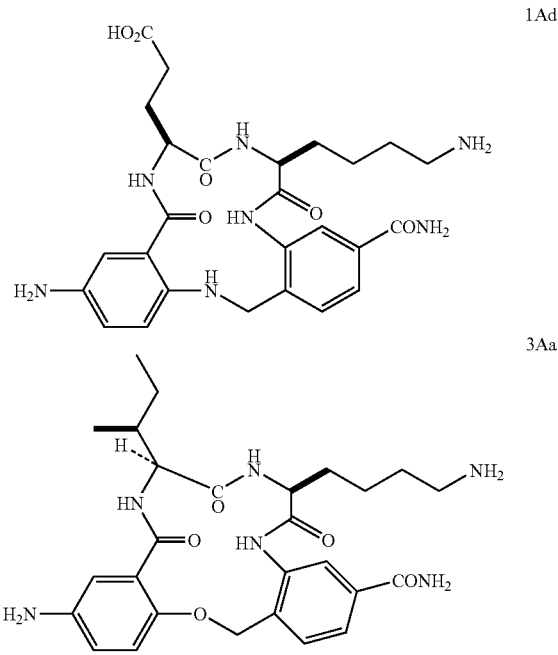

3Ak
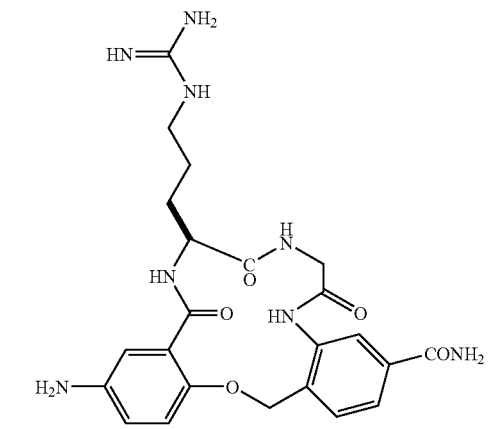
3Ba
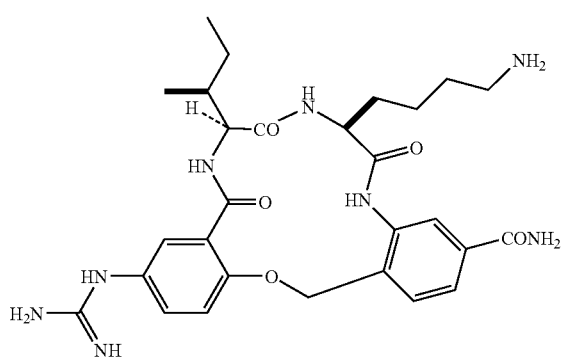
3Bg
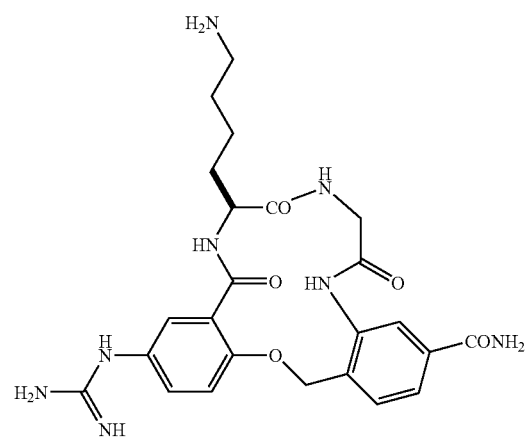
3Bi
3Ca
3Ce
3Cg
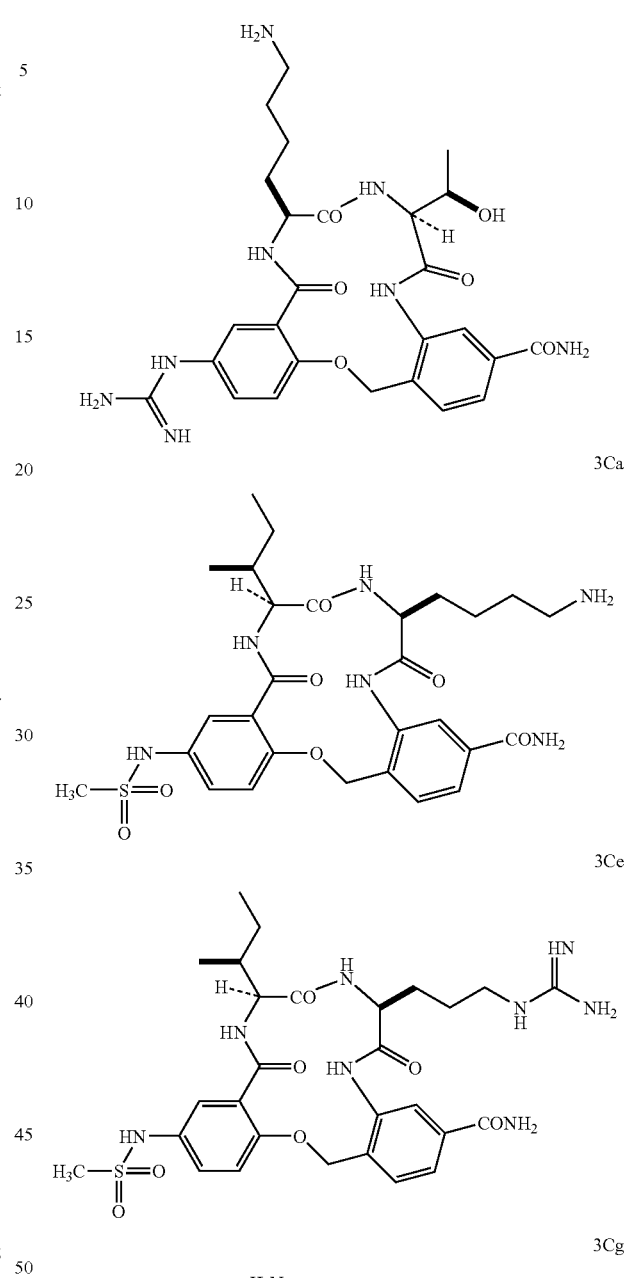
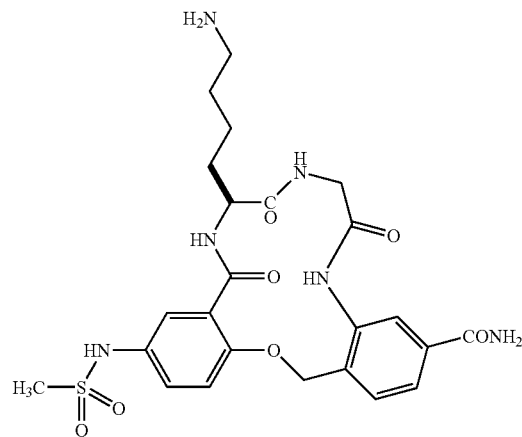

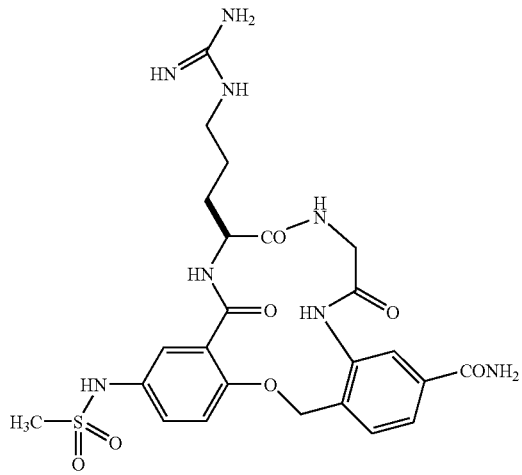

3Ck

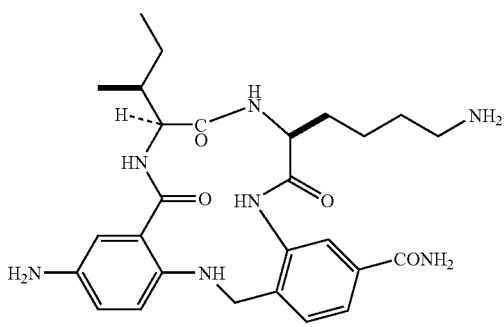

1Aa

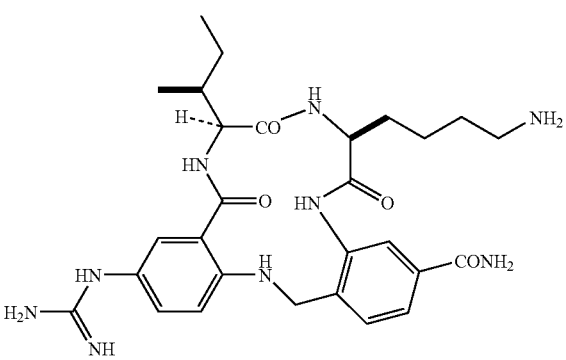

1Ba

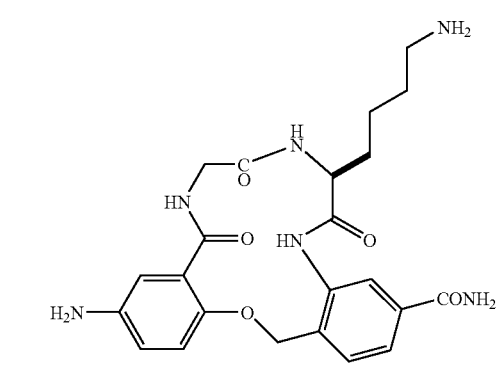

3Ac

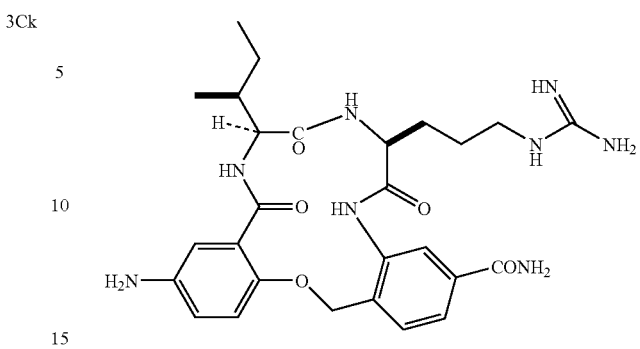

3Ae

The invention also relates to a method of treating or preventing RGC death and/or glaucoma in a subject by administering to the subject an effective amount of a neurotrophin receptor-regulating composition comprising at least one molecule that is a TrkA receptor agonist, a TrkC receptor agonist, a p75 receptor antagonist or a compound that is a combination of the foregoing (e.g., an agonist or antagonist of two or more neurotrophin receptors (e.g., a TrkA and TrkC agonist)) and a suitable pharmaceutical carrier. In particular embodiments, the TrkA receptor agonist, TrkC receptor agonist and p75 receptor antagonist are the β-turn cyclic compounds described above. In other embodiments, the method further comprises administering at least one intraocular pressure normalizing drug and/or an IPREG-regulating composition with the neurotrophin receptor-regulating composition.

The methods of the invention overcome the disadvantages of current glaucoma therapies in that the agents described herein are specific, selectively targeting Trk receptors and/or the p75 receptor and, in doing so, are more effective. Furthermore, the compounds and/or molecules for use in the treating RGC death and/or glaucoma are relatively stable and easy to administer.

BRIEF DESCRIPTION OF THE DRAWINGS

FIG. 1A is the code for the β-turn backbones, numbered 1, 2 and 3, for TrkC receptor agonists.

FIG. 1B is the code for X-substituents of the backbone, lettered A, B, C and D, for TrkC receptor agonists.

FIG. 1C is the code for dipeptide $R^1$ and $R^2$ substituents of the backbone for the TrkC receptor agonists.

FIG. 1D illustrates the complete letter codes for TrkC receptor agonist compounds including the backbone (1, 2 or 3), X-substituents (A, B, C or D) and dipeptide amino acids ($R^1$ and $R^2$).

FIG. 2 is a graph illustrating the effect of betaxolol in reducing high intraocular pressure (IOP).

FIG. 3 illustrates the experimental procedure used to test the effectiveness of various pharmacological treatments on RGC death.

FIG. 4 is a series of micrographs of retinal RGCs after induction of high IOP in response to betaxolol and/or the TrkA agonist D3.

DETAILED DESCRIPTION OF THE INVENTION

The methods of the present invention relate to the use of modulators (e.g., agonists, antagonists) of neurotrophin receptors (e.g., TrkA, TrkC, p75) to treat and/or prevent retinal ganglion cell (RGC) death and/or glaucoma. It is this RGC death that is responsible for glaucoma progression and the associated loss of vision. Trk receptor (e.g., TrkA, TrkC) agonists can function to provide necessary trophic support to RGCs and prevent their death. Further, antagonism of the p75 receptor (via e.g., antagonism of the p75 receptor itself or TrkC), inhibits presumptive p75 receptor-mediated death of RGCs in glaucoma.

The neurotrophin receptor modulators for use in the claimed methods can be any molecule and/or pharmacological agent that selectively induces one or more activities (e.g., agonist) or inhibits one or more activities of a particular neurotrophic receptor. These receptor activities include, for example, potentiation of ligand (e.g., NGF, NT-3 or BDNF)-mediated receptor response, receptor tyrosine phosphorylation, receptor signaling and/or activation/phosphorylation of interacting/downstream signaling molecules of the neurotrophin receptors, promotion of cell growth and survival (trophic activity) or differentiation (neuritogenic activity). The compound/molecule (e.g., compound, peptide) used in the methods is preferably one that is effective in the treatment of humans/mammals (e.g., capable of crossing the blood brain barrier to reach CNS targets and easily delivered), has minimal side effects (e.g., non-immunogenic, non-pleiotropic, acceptable pharmokinetics) and has a reasonable stability and/or half-life. Thus, the neurotrophin receptor modulator can be an antibody, peptide, protein, gene, molecule, chemical compound, antibody mimetic, mimetic peptide and/or peptidomimetic. In a particular embodiment, the neurotrophin receptor modulators are mimetic peptides or peptidomimetic compounds, specifically, cyclic compounds which, by design, mimic the β-turn region of neurotrophin receptor ligands (e.g., NGF or NT-3). Advantageously, these cyclic β-turn molecules are small and stable (e.g., resistant to proteolysis), so that they are easily delivered and able to easily access the neurotrophin receptor(s) targeted.

For instance, selective activation of the TrkA receptor, the signaling of which promotes cell survival, has been found to effectively prevent RGC apoptosis, in particular, in concert with the use of an intraocular pressure-normalizing drug. TrkA receptor agonists may protect RGCs from apoptosis resultant from various ocular insults including optic nerve damage and glaucoma. Accordingly, the present invention relates to a method of treating or preventing RGC death or glaucoma in a subject by administering to the subject an effective amount of a composition comprising a TrkA receptor agonist and a suitable pharmaceutical carrier and, in addition, at least one intraocular pressure-normalizing drug. As used herein, "a subject" to which a composition for use in the methods is administered is any animal having or having the possibility of being afflicted with RGC apoptosis and/or glaucoma. The subject is preferably a mammal and most preferably a human. In one embodiment, the TrkA receptor agonist is an antibody which inhibits binding of NGF to the receptor (e.g., monoclonal antibody (mAb) 5C3 (see LaSauteur L. et al., *J Neuroscience* 16:1308-1316, 1996)). In a particular embodiment, the cyclic compound is a β-turn peptidomimetic cyclic compound having a macrocyclic ring of about 13 to 17 atoms. In a further embodiment, the macrocyclic ring is formed predominantly by a carbon and nitrogen backbone and has one or more amino acid side chains that extend from this backbone. These side chains give the β-turn peptidomimetic cyclic compound the ability to mimic NGF as they correspond to residues naturally found within the β-turns of NGF. There are a number of β-turn peptidomimetic cyclic compounds effective in acting as agonists of the TrkA receptor (e.g., D3, D53b-d, D21, P23 and P58) and these agonists are described in detail in U.S. Pat. No. 6,881,719, which is herein incorporated by reference.

In a particular embodiment of the present invention, the compound is a β-turn peptidomimetic cyclic compound of formula (I):

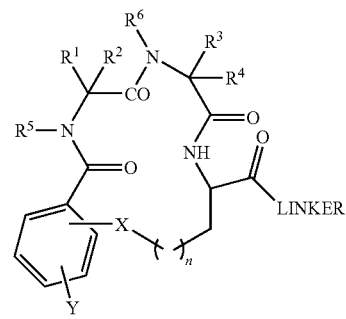

wherein $R^1$ and $R^3$ are selected from hydrogen, $C_1$ to $C_6$ alkyl or aryl substituents found in a natural or unnatural amino acid; $R^2$ and $R^4$ are hydrogen or alkyl; $R^5$ and $R^6$ are hydrogen; $R^1$ and $R^2$ or $R^3$ and $R^4$ together with the carbon atom to which they are attached form a cyclopropyl, cyclobutyl, cyclopentyl or cyclohexyl group; Y is hydrogen or one or two aromatic substituents; X is selected from O, N, S, P, Se, C, alkylene of 1 to 6 carbon atoms, SO, $SO^2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$ and CHO. Another suitable LINKER group is NH—$CH_2$—COOH.

In another embodiment, X is O, S or NH, $R^1$, $R^3$, $R^5$ and $R^6$ are each hydrogen atoms and the macrocyclic ring has 14, 15 or 16 ring atoms.

In another embodiment of the present invention $R^1$ and $R^3$ are derived from a sequence of different amino acids side chains selected from natural and synthetic amino acids.

In yet another embodiment of the present invention X is O, S or NH.

In a preferred embodiment, the TrkA receptor agonist is the β-turn peptidomimetic cyclic compound of the formula:

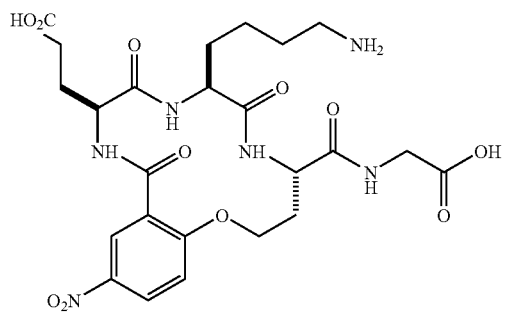

known as "D3" (see Maliartchouk et al., *Mol Pharmcol* 57(2): 385-391, 2000 and U.S. Pat. No. 6,881,719), or derivatives of D3. A number of derivatives of D3 are envisioned for use in the methods of the invention and include simple modifications like biotinylated forms and molecules wherein two such units are linked by dimers. Other derivatives of D3 include side chains $R^1$-$R^6$ having any alkyl or aryl substituent found in natural and unnatural amino acids.

The side chains typical of the protein amino acids (e.g., Arg, Trp, His) allow for the formation/design of a diversity of structures that are easily generated derivatives of D3, and they can include many types of functional groups. The constituent amino acids may be N-alkyl, N-aryl, α,α-dialkyl, and cyclic derivatives such as might be formed from cyclopropane amino acids.

The substituent(s) Y may be hydrogen or one or two aromatic substituents for example nitro, amino, halo, alkyl for example alkyl of 1 to 6, preferably 1 to 4 carbon atoms, and aryl for example phenyl or naphthyl. The alkyl and aryl substituents Y may be unsubstituted or substituted, suitable substituents being nitro and alkyl of 1 to 6 carbon atoms.

Y may also be derivatized with a functional group, for example biotin. The group X may be any nucleophilic atom like O, N, S, P, Se, but also others such as C, or may be an alkylene radical typically of 1 to 6 carbon atoms, for example methylene; or NH. The point of connection could be ortho- or meta- to the benzoyl carbonyl. Permissible values of "n" are 0, 1, 2, 3, 4, and 5. The linking side chain that incorporates X may be aliphatic as indicated in structure (I) aromatic or heteroaromatic.

The side chain alkyl groups $R^1$, $R^2$, $R^3$, $R^4$, $R^5$, and $R^6$ can be varied in many ways to enhance the biological activities of these materials. Typically $R^1$, $R^2$, $R^3$, and $R^4$ are amino acid side-chain substituents found in the twenty protein-amino acids or side-chains very similar to these, for example the side-chains of glutamic acid, lysine, ornithine and threonine, in either enantiomeric configuration. If the $R^1$ substituent is an amino acid side chain, the other substituent on that carbon, $R^2$, will typically be hydrogen, but could also be methyl, ethyl or benzyl. Alternatively, $R^1$ and $R^2$ could be joined as in cyclopropane, cyclobutane, cyclopentane, and cyclohexane, residues. $R^3$ and $R^4$ are related in the same way as $R^1$ and $R^2$ as described above. That is, one of them will be an amino acid side chain or something very similar. The other of these two substituents is hydrogen in most cases, but could also be methyl, ethyl, propyl, benzyl or some simple alkyl system as described above.

There is much scope for variation in $R^5$ and $R^6$ with the most common substituent at these positions being hydrogen. Those substituents can also be designed to correspond to one of the side chains of the twenty protein-amino acids, in particular, methyl.

The compounds (I) are more especially compounds prepared from the twenty protein amino acids or simple analogs of these, including their enantiomers, N-alkyl, N-aryl, α,α-dialkyl, and cyclic amino acids. Side chains found to be particularly conducive to biological activities are $R^1$ and $R^3$ as side chains of lysine, glutamic acid, tyrosine, iso-leucine, asparagine, and threonine, $R^2$, $R^4$, $R^5$, and $R^6$ as hydrogen. One or more of the side chains are selected especially to correspond to side chains within the turn regions of NGF.

In general, the macrocyclic compounds have 13 to 16 membered rings where the X substituent is O, N, S, SO, or $SO_2$.

The present invention also relates to a method of treating or preventing RGC death or glaucoma with the TrkA agonist compounds described above. Thus, the method comprises treating RGC death or glaucoma by administering to a subject an effective amount of a TrkA receptor agonist comprising a β-turn peptidomimetic cyclic compound having a macrocyclic ring of 13 to 17 carbon atoms and a suitable pharmaceutical carrier. As before, the macrocyclic ring can have one or more side chains extending from the backbone ring atoms, that, in one embodiment correspond to the β-turns of NGF. In a particular embodiment the β-turn peptidomimetic cyclic compound has the formula:

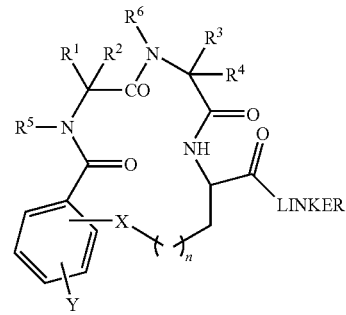

wherein $R^1$ and $R^3$ are selected from hydrogen, $C_1$ to $C_6$ alkyl or aryl substituents found in a natural or unnatural amino acid; $R^2$ and $R^4$ are hydrogen or alkyl; $R^5$ and $R^6$ are hydrogen; $R^1$ and $R^2$ or $R^3$ and $R^4$ together with the carbon atom to which they are attached form a cyclopropyl, cyclobutyl, cyclopentyl or cyclohexyl group; Y is hydrogen or one or two aromatic substituents; X is selected from O, N, S, P, Se, C, alkylene of 1 to 6 carbon atoms, SO, $SO^2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$ and CHO. Another suitable LINKER group is NH—$CH_2$—COOH. Further, the X can be 0, S or NH, $R^1$, $R^3$, $R^5$ and $R^6$ are each hydrogen atoms and the macrocyclic ring has 14, 15 or 16 ring atoms, the $R^1$ and $R^3$ can be derived from a sequence of different amino acids side chains selected from natural and synthetic amino acids and more particularly, the X is O, S or NH.

In a preferred embodiment the Trk A receptor agonist for use in the method is the compound D3 having the formula:

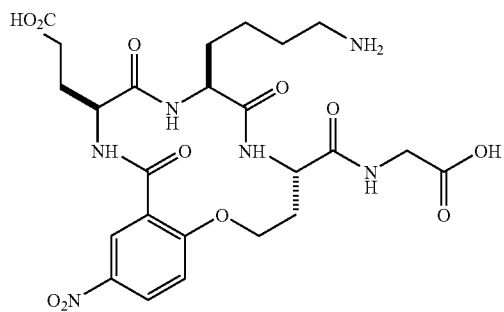

and derivatives thereof.

TrkC is yet another Trk receptor family member associated with glaucoma and RGC death. There is an early and sustained increase in TrkC expression, specifically, that of the truncated isoform of TrkC, in retinal glial cells (Müller cells) with ocular hypertension (see Rudinski et al., *J. Neurobiol* 58:341-354, 2004). The end feet processes of these Müller cells sense the vitreal environment and act in a paracrine manner to support RGCs. Generated by alternative splicing, the truncated isoform of TrkC lacks the TrkC kinase domain and, consequently, kinase activity and the concomitant catalytic activities of full-length TrkC receptors (see, e.g, Tsoulfas P et al., *Neuron* 10:975-990, 1993 and Valenzuela D M et al., *Neuron* 10:963-974, 1993). The non-catalytic, truncated TrkC receptors are believed to sequester neurotrophins and, further, inhibit signaling of active catalytic TrkC receptors (see e.g., Palko M E et al., *J Neuroscience* 19:775-782, 1999).

Thus, TrkC agonists and antagonists can be used in the methods of treating or preventing glaucoma and RGC death. TrkC agonists could be used to activate full-length TrkC receptors and induce survival and/or protective factors that can rescue RGCs from the apoptosis induced by ocular hypertension. In contrast, the up-regulation of truncated TrkC, which lacks the kinase domain, in Müller cells could be a contributing factor to RGC death. These catalytically inactive TrkC receptors, still able to bind NT-3, could decrease the availability of NT-3 for RGCs, which may be detrimental to RGCs already depleted of trophic support due to poor retrograde transport of growth factors. Thus, TrkC antagonists can be used in the methods to inhibit neurotrophin (e.g., NT-3) binding to the truncated form of the TrkC receptor, increasing neurotrophin availability for RGCs. In addition, TrkC can also regulate p75 function (Hapner S J et al., *Dev Biol* 201: 90-100, 1998) and, under conditions of ocular hypertension, full-length TrkC may enhance and/or activate p75 receptor-mediated RGC apoptosis. A TrkC antagonist could be used to inhibit this TrkC-mediated apoptotic activation of the p75 receptor.

Accordingly, the present invention also relates to a method of treating or preventing RGC death and/or glaucoma in a subject by administering to the subject an effective amount of a composition comprising a TrkC receptor agonist or TrkC receptor antagonist and a suitable pharmaceutical carrier. In a particular embodiment, the TrkC receptor agonist is able to stimulate one or more activities of and/or enhance neurotrophin interaction with the full-length TrkC, whereas a TrkC receptor antagonist is able to inhibit one or more activities of or prevent neurotrophin interaction with full-length and/or truncated TrkC. A TrkC receptor agonist or antagonist that is used in the methods can be a gene, protein, polypeptide, antibody, peptidomimetic or the like, as described above. In one embodiment, the TrkC receptor agonist is an antibody (e.g., mAb 2B7 (see Pattarawarapan M et al., *J Med Chem* 45:4387-4390, 2002)). In another embodiment, the TrkC receptor agonist is a β-turn cyclic compound. In yet another embodiment, the TrkC receptor agonist is a compound comprising a cyclic amino, ether or sulfide scaffold (see FIG. 1A), with various substituents (e.g., amine, guanidine or MeSO₂NH) (see FIG. 1B) and R¹ and R² groups comprising dipeptide amino acid fragments (see FIG. 1C). (See also FIG. 1D). In accordance with a particular aspect of the method, the TrkC receptor agonist is a β-turn cyclic compound selected from the group consisting of:

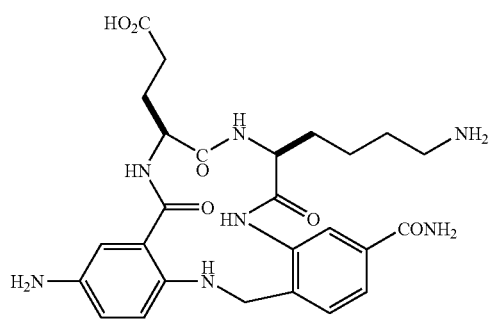

1Ad

-continued

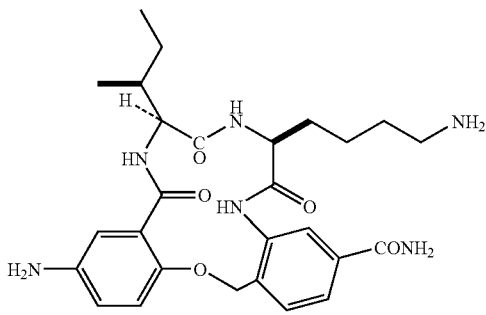

3Aa

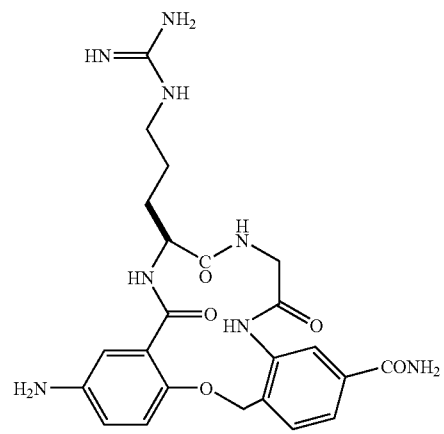

3Ak

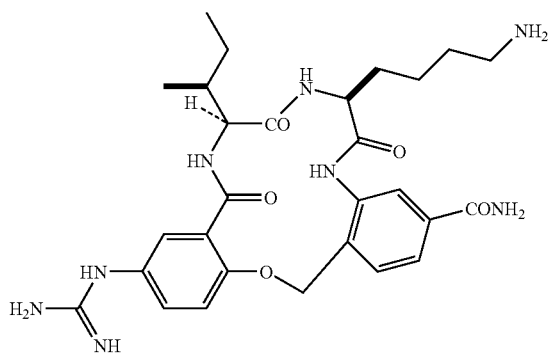

3Ba

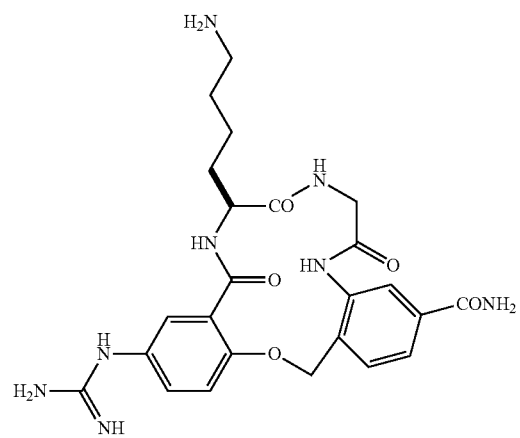

3Bg

-continued
3Bi
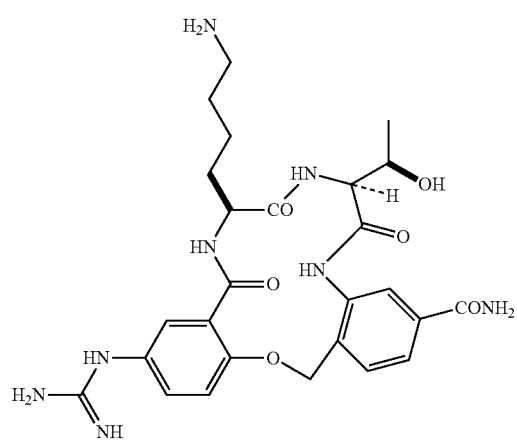
3Ca
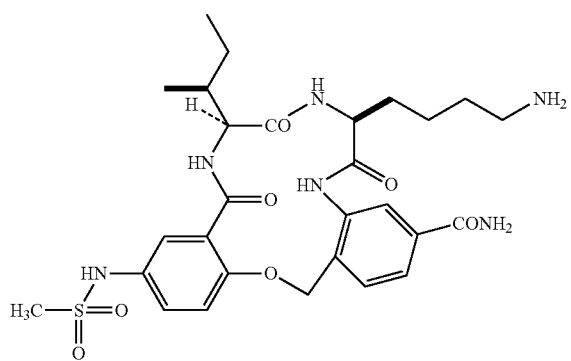
3Ce
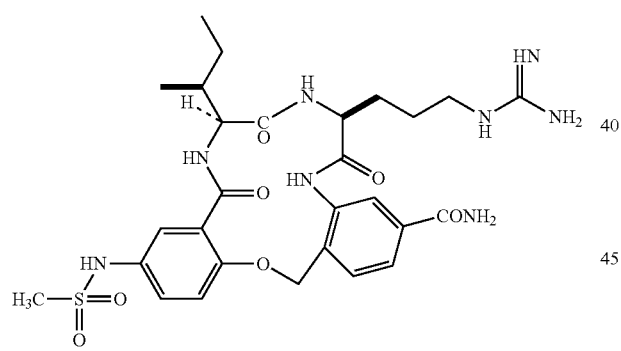
3Cg
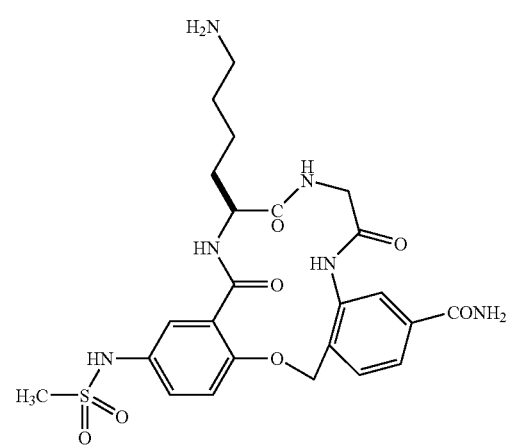
-continued
3Ck
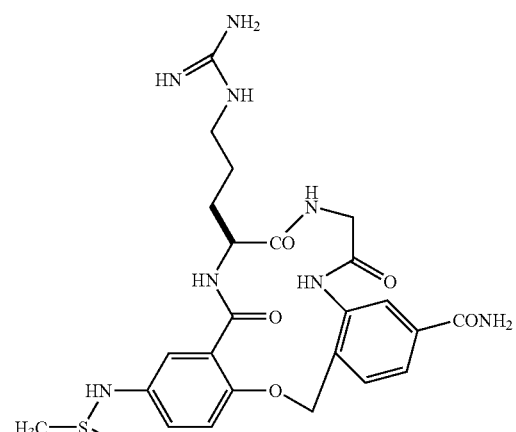
1Aa
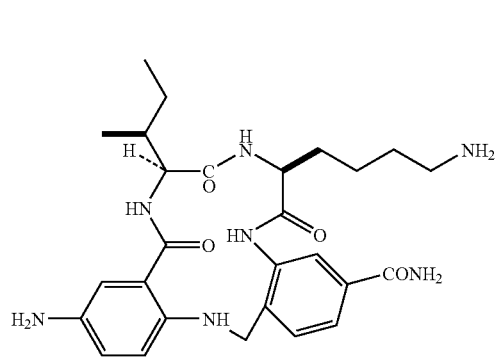
1Ba
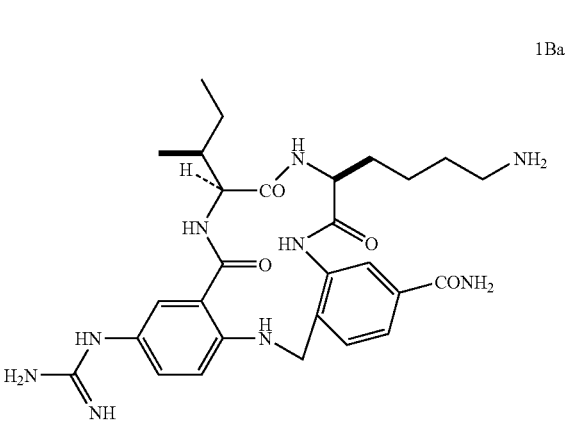
3Ac
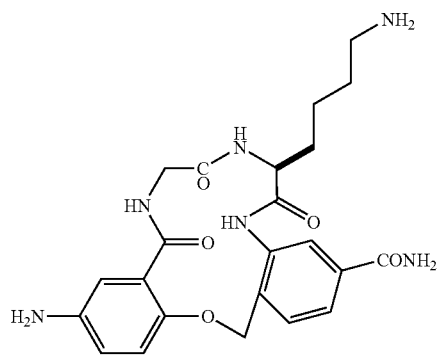

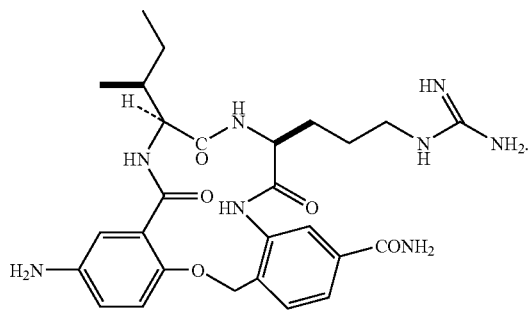

3Ae

According to the methods of the invention, an effective amount of a composition comprising a TrkA receptor agonist and/or a TrkC receptor agonist or a TrkC receptor antagonist is administered to a subject by an appropriate route and can be administered either alone or in conjunction with another drug (e.g., an intraocular pressure-normalizing drug) or other appropriate molecule/compound. An effective amount of the composition is an amount sufficient to achieve the desired therapeutic or prophylactic effect, under the conditions of administration. For example, the amount of the composition administered is one such that RGC apoptosis and, consequently, glaucoma progression is lessened and/or arrested. This amount could be, for instance, about 0.1 to 100 mg/kg body weight of a patient of a β-turn cyclic compound (e.g., neurotrophin receptor modulating compound) for treatment of a human subject. Administration of the compound(s) at this concentration would generally require that about 100 to 200 milligrams of the β-turn cyclic compound be present in the composition. The compositions may be concentrated and diluted for use, with those suitable for dilution typically containing about 90 percent or more of the compound by weight.

These compositions comprising the Trk receptor modulators (e.g., a peptidomimetic, gene, antibody) are further comprised of a suitable pharmaceutical carrier, the formulations varying according to the route of administration selected and this route of administration influenced by or selected based on the solubility, stability and half-life of the compounds. Suitable pharmaceutical carriers can also contain inert ingredients which do not interact with the regulatory/active substances in the compositions. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate, dextrose, ethanol, surfactants such as glycerol, or excipients.

The compositions are preferably administered in the suitable pharmaceutical carrier in any effective or convenient manner including by intraocular injection, topical conjunctival application, topical corneal application or through the use of a mechanical delivery device. The composition can be administered in a single dose or in multiple doses to ensure that the patient sustains therapeutically significant levels of the compositions during a treatment regimen. The dosage can be determined by the skilled clinician using methods known in the art and will be dependent on the particular compound(s) chosen for the composition, the subject's age, body weight, environment, genetic factors, sensitivity and tolerance to drugs and overall well-being. In therapy or as a prophylactic, the active agents may be administered to a subject as an injectable composition, for example as a sterile aqueous dispersion, preferably isotonic, or "packaged" as liposomes or microspheres. Thus, when injectable compositions are desired, the Trk receptor modulators may be formulated, for example, into preparations for injection by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives. The active ingredient may also be in powder form for reconstituting with a suitable vehicle prior to administration. If, as in one embodiment, the composition is for topical ocular use, the formulation can be suitable for that type of administration (e.g., sterile, non-irritating/toxic).

The composition can also be formulated for topical application, for example, in the form of ointments, creams, lotions, eye ointments and, most preferably, eye drops or eye gels and can contain the appropriate conventional additives, including, for example, preservatives, solvents to assist drug penetration, and emollients in ointments and creams. Such topical formulations can also contain compatible conventional carriers, for example cream or ointment bases, and ethanol or oleyl alcohol for lotions. Alternatively, if an adequate means of delivery, the composition comprising the TrkA receptor agonist can be formulated for oral administration using pharmaceutically acceptable tableting excipients including lactose, microcrystalline cellulose, corn starch, stearic acid, or the like, can be used, if desired, to prepare such dosage forms. Oral administration can also comprise a liquid composition formulated in water, glycols, oils, alcohols or the like.

The findings disclosed herein indicate that combining a selective Trk receptor modulator (e.g., TrkA agonist, TrkC agonist) with an intraocular pressure-lowering drug is highly effective at preventing RGC loss. Accordingly, the methods of the present invention also comprise the administration of at least one of a number of intraocular pressure-normalizing drugs. Intraocular pressure-normalizing drugs include parasympathomimetic/cholinergic agents (e.g., pilocarpine, aceclidine, carbachol), sympathomimetic agents (e.g., epinephrine, dipivefrin, alpha-selective adrenergic agonists), sympatholytic agents (e.g., beta blockers (e.g., timolol, betaxolol, levobunolol, carteolol, metipranolol)), carbonic anhydrase inhibitors (e.g., acetazolamide, methazolamide, dichlorfenamide, dorzolamide, brinzolamide), prostaglandin analogs (e.g., latanoprost, travoprost bimatoprost), docosanoids (e.g., unoprostone) and osmotic agents. At least one intraocular pressure-normalizing drug can be administered in the methods of the invention (monotherapy) and, if desired/necessary, more than one agent can be given. In the instance more than one intraocular pressure-normalizing drug is used, a combination of drugs in various classes is generally administered (e.g., timolol and dorzolamide or timolol and latanoprost). The amount of the intraocular pressure-normalizing drug administered will vary depending on the size, age, body weight, general health, sex, and diet of the subject (e.g., human or other animal), the time of administration, the biological half-life of the particular drug, the level of severity of the ocular hypertension and the amount of the β-turn peptidomimetic cyclic compound used/necessary. Adjustment and manipulation of established dose ranges are well within the ability of those of skill in the art, and preferably the dosage minimizes side effects and toxicity. For example, in a particular embodiment, the intraocular pressure-normalizing drug is betaxolol which can be administered in an ophthalmic suspension of 0.25% (e.g., betaxolol HCl) to a human subject, for instance.

The intraocular pressure-normalizing drug and Trk receptor-modulating composition can be administered at intervals dependent on several factors, including the level and/or stage of glaucoma, and this dosing schedule is best assessed by one of skill in the art for a particular patient. In one embodiment, an effective amount of the intraocular pressure-normalizing drug is administered once or twice per day (i.e., in a 24 hour period). Depending on the pharmaceutical carrier for the compound or molecule used and, likewise, the route of administration, it may be desirable and/or necessary to administer the compounds simultaneously (i.e., concurrently) as either separate pharmaceutical excipients or as one joint composition. For example, the drug and compounds can be administered topically or injected intraocularly (e.g., to a non-human animal). Alternatively, the chosen intraocular pressure-normalizing drug and Trk receptor-modulating compound can be administered sequentially, that is, as separate compositions administered one after the other. The amount of time between administration of each composition will vary according to a patient's tolerance of the compounds and therapeutic need(s). Generally, an intraocular pressure-normalizing drug would be administered to a patient regularly (e.g., daily) and the neurotrophin receptor-modulating compound administered on a schedule designed for optimal treatment response/results (e.g., based on the half-life of the compound and the level of severity of patient symptoms). The skilled clinician can adjust and/or vary the dosing order or schedule to treat a patient most effectively.

The methods of the invention for treating or preventing RGC death, and/or glaucoma can also be further comprised of administering an effective amount of a p75 receptor antagonist. The p75 receptor is believed to have a role in RGC apoptosis (see e.g., Khursigara et al. *J Biol Chem* 274:2597-2600). Although it was found herein that, alone, a selective p75 receptor antagonist had no effect on RGC apoptosis, it is likely that specific activation of a Trk receptor(s) together with inhibition of the p75 receptor would be combinatorial or synergistic in preventing RGC death and/or treating glaucoma. The p75 receptor antagonist for use in the method can be any composition that specifically inhibits p75 receptor signaling/activity as described previously for neurotrophin receptor modulators (e.g., compound, molecule, protein, peptide or peptidomimetic) including, for example, an antibody (e.g, mAb NGF30 (see Saragovi et al., *J Biol Chem* 273:

34933-34940, 1998)). Due to their effectiveness and overall ease of administration, in a particular embodiment, the p75 receptor antagonist administered is also one or more β-turn cyclic compounds which are shown in Table 1.

TABLE 1

β-turn cyclic p75 receptor antagonists

| Analog amino acid sequence | Original structure/ amino acid residues | Analog code |
|---|---|---|
| CKGKEC | β-turn 32-35 | C (32-35) (SEQ ID NO: 1) |
| CDIKGKEC | β-turn 30-35 | C (30-35) (SEQ ID NO: 2) |
| CTAIKGKEC | β-turn 29-35 ΔD30A | C (29-35 ΔD30A) (SEQ ID NO: 3) |
| CIKGKEC | β-turn 31-35 | C (31-35) (SEQ ID NO: 4) |
| YCATDIKGKECY | β-turn 28-35 | C (28-35) (SEQ ID NO: 5) |

These p75 receptor antagonists mimic the A-A" loop of NGF. Oxidation of the cysteine (Cys) residues in the peptide results in the formation of a Cys-Cys disulfide bond, causing cyclization of the molecules (see LeSauteur et al., *J Biol Chem* 270(12):6564-6569, 1995). The p75 receptor antagonist can be administered in a suitable pharmaceutical carrier as described above (e.g., sterile water, physiological saline, bacteriostatic saline, phosphate-buffered saline, Hank's solution, Ringer's lactate, dextrose, ethanol, surfactants or excipients) and, depending on the composition of the pharmaceutical carrier, can be administered topically, orally, intravenously, intraperitoneally, intramuscularly, subcutaneously, intranasally, transdermally or intradermally among other suitable administration routes. Preferably, the p75 receptor antagonist is administered locally to the eye, most preferably through the use of eye drops, an eye gel or eye ointment. The p75 receptor antagonist can be administered in an amount/dose best determined by the skilled clinician, on the same or similar schedule as the other Trk receptor modulators (e.g., Trk A and Trk C) and, further, the compounds/molecules can be administered alone (e.g., sequentially) as separate pharmaceutical excipients or in conjuction (e.g., concurrently or simultaneously) as one joint composition according to a patient's tolerance of the antagonist/agonist and therapeutic need. The p75 receptor antagonist can be administered during a treatment regimen involving one or more Trk receptor modulators (e.g., TrkA receptor agonist, TrkC receptor agonist, TrkC receptor antagonist) and one or more intraocular pressure-normalizing drugs (e.g., betaxolol).

A method is also provided for treating or preventing RGC death or glaucoma in a subject using one or more of the aforementioned neurotrophin receptor-modulating compositions. Thus, the method comprises administering to a subject an effective amount of a composition comprising one or more compounds/molecules selected from the group consisting of a TrkA receptor agonist, a TrkC receptor agonist, a TrkC receptor antagonist, a p75 receptor antagonist and/or a compound that is a combination of the foregoing (a compound that acts, e.g., as both a TrkA agonist and a TrkC agonist) and a suitable pharmaceutical carrier. The compositions comprising the agonists and/or antagonists are as discussed previously, in a pharmaceutical carrier that is an acceptable and effective formulation for the particular route of administration. Further, if more than one of the molecules are used in the method, the compositions can be administered by one or more routes sequentially (e.g., a TrkA agonist, then a TrkC agonist, then a p75 antagonist), simultaneously (e.g., in one composition comprising a TrkA agonist, TrkC agonist and a p75 antagonist) or using a combination of the two routes (e.g., a TrkA agonist, then one composition comprising a TrkC antagonist and a p75 antagonist). Like previous methods, the method can further comprise the administration of at least one of the intraocular pressure normalizing drugs described previously. The TrkA receptor agonist, TrkC receptor agonist and p75 receptor antagonist are as described above and, in a particular embodiment, are the β-turn cyclic compounds described previously. In one aspect of the method, compounds that can act as both TrkA and TrkC receptor agonists for use in the method can include the β-turn cyclic compounds 3Ac, 3Ae, 3Ak, 3Ca, 1Aa, 1Ad. The structure of these compounds is also shown below:

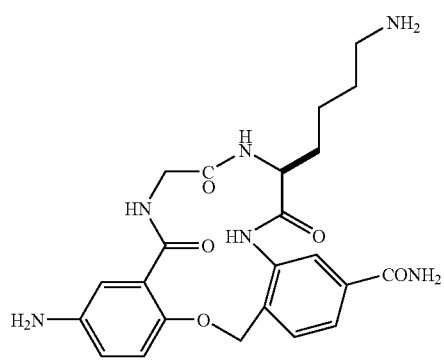

3Ac

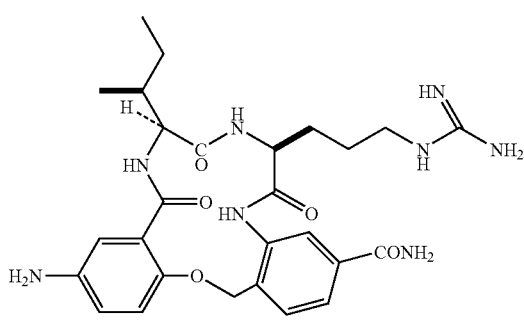

3Ae

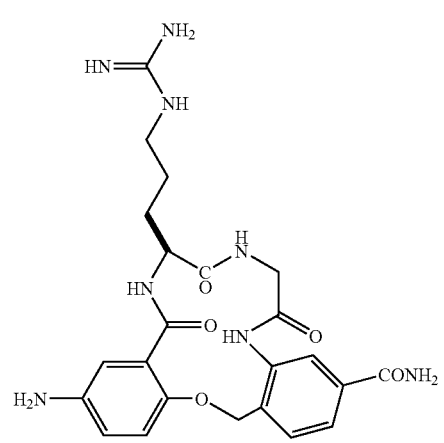

3Ak

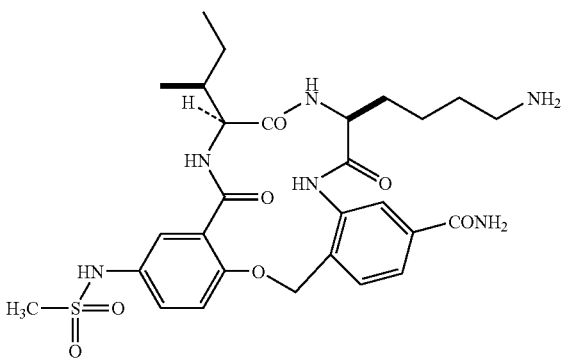

3Ca

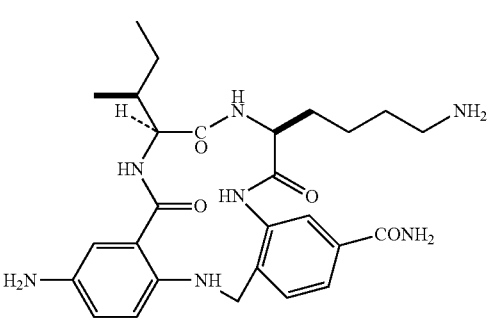

1Aa, 1Ad

A subject having glaucoma and/or RGC death could, if desired or necessary, also be further treated with other drugs, molecules or compounds that treat or prevent RGC apoptosis and glaucoma. For example, several genes termed intraocular pressure-regulated genes (IPREGs) having significantly and specifically altered (increased, reduced) expression due to high intraocular pressure (IOP) and thought to be relevant to and/or involved in cell signaling and cell death have been identified (see International Application No. PCT/US2006/045169, filed Nov. 22, 2006 and published as WO 2007/062101 A2 on May 31, 2007, herein incorporated by reference). These genes were identified using a rat model of ocular hypertension, with altered gene expression elucidated using a gene microarray. Genes determined to be IPREGs (e.g., those likely to be involved in ocular degeneration) met one or more specific criteria (e.g., specific and early induction by high IOP, sustained expression after induction and/or with the normalization of high IOP and those believed to have a role in cell death, survival or associated signaling). The known genes identified include: α2 macroglobulin, PSD-95/SAP90-associated protein-4, Reggie1-1, RBCK, Gzα, Protein phosphatase 1 gamma, Ribosomal protein L23-related product, Gial fibrillary acidic protein, Cyclic nucleotide-gated cation channel, SPARC, B-2 arylamine N-acetyltransferase, Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase, Asparagine synthase. Thus, for example, the expression of the IPREG α2 macroglobulin was found to be up-regulated in response to high IOP and neutralizing antibodies to α2 macroglobulin resulted in significantly decreased RGC apoptosis.

Accordingly, a composition that inhibits the activity and/or expression of one or more IPREGs upregulated (e.g., α2 macroglobulin, PSD-95/SAP90-associated protein-4, Reggie1-1, RBCK, Gzα, Protein phosphatase 1 gamma, Ribosomal protein L23-related product, Gial fibrillary acidic protein, Cyclic nucleotide-gated cation channel, SPARC and B-2 arylamine N-acetyltransferase) and/or a composition that increases the expression and/or activity of one or more IPREGs down-regulated (e.g., Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase and Asparagine synthase) by high IOP can be administered with the neurotrophin receptor modulator(s) used in the methods of the invention. The IPREG-regulating composition can comprise inhibitory compounds/molecules (e.g., small interfering RNAs (siRNAs), antisense oligonucleotides, neutralizing antibodies, small molecules, recombinant gene expression vectors, recombinant gene viral vectors, synthetic peptides, recombinant polypeptides, peptidomimetics and inhibitors (e.g., peptides, genes, vectors) of the regulatory regions of upregulated IPREGs) and/or activating or expression-inducing compounds/molecules (e.g., siRNAs, antisense oligonucleotides and neutralizing antibodies to negative regulators of down-regulated IPREGs, small molecules, recombinant gene expression vectors, recombinant gene viral vectors, synthetic peptides, recombinant polypeptides, peptidomimetics and activators of the regulatory regions of downregulated IPREGs).

For administration to a subject, the composition comprising an IPREG-regulating substance (e.g., compound, molecule), can also be comprised of a suitable pharmaceutical carrier, like those discussed previously. The IPREG-regulating composition would likely be administered at a dosage and on a schedule determined by one of skill in the art to complement (combine or synergize with) the treatment of the patient with the neurotrophin receptor modulating composition and intraocular pressure-normalizing drug. The IPREG-regulating composition can be administered by the various routes described above (e.g., intraocular injection, topical conjunctival application, topical corneal application, mechanical delivery device) and is also preferably administered locally to the eye (e.g., through eye drops, ointments, gels or creams).

Any combination of the aforementioned compositions can be used, as deemed necessary by the skilled clinician, for a complete/effective therapy of glaucoma or RGC death. Thus, together with the Trk receptor modulators, an intraocular pressure-normalizing drug and/or a p75 receptor antagonist and/or an IPREG-regulating composition can be administered to a subject in need thereof (e.g., a subject having RGC apoptosis and/or glaucoma). A specific treatment regimen would be tailored to a particular patient, determined by, for example, disease stage, severity, any known underlying disease mechanisms and patient tolerability of use of two or more of the above described compositions.

EXEMPLIFICATION

Example 1

Experimental Model of Ocular Hypertension

Induction and Regulation of High Intraocular Pressure

High IOP was induced in rat eyes, by reducing aqueous humor outflow through episcleral vein cauterization, while the contralateral eyes were sham-operated and were used as controls (FIG. 2). The IOP of cauterized eyes was significantly higher than control contralateral eyes after vein cauterization (p≤0.01). The mean IOP in glaucomatous eyes was ~21 mm Hg compared with a mean IOP of ~12.6 mm Hg in normal eyes. Daily topical treatment with betaxolol starting at day 4 post-cauterization lowered aqueous humor production and reduced high IOP to normal levels within 3 days, but had no significant effect on the normal IOP of non-cauterized contralateral eyes. There were no significant differences in the IOP of cauterized eyes treated with betaxolol versus control normal IOP eyes with or without betaxolol.

Chronic RGC Death Induced by High IOP and Maintenance After IOP Normalization

Using retrograde tracers, surviving RGCs were labeled at the cell soma and flat retinal spreads were analyzed for RGC numbers (Table 2). Rat eyes were cauterized and they were either left untreated, or their high IOP was normalized by treatment with daily betaxolol starting at day 4 until the endpoint day 42.

RGC loss in ocular hypertension was time-dependent. At days 21 and 42 post-cauterization there was an average RGC loss of ~16% and ~35% respectively if the cauterized eyes were not treated with betaxolol. In contrast, if eyes were treated daily with betaxolol, at days 21 and 42 post-cauterization there was an average RGC loss of ~7% and ~20% respectively as shown in Table 2.

Table 2. Reduction of Ocular Hypertension Only Partially Prevents RGCs Death in Glaucoma.

Each data point represents the average of 3-4 retinas/experimental group±standard deviation (sd). At the indicated day post-cauterization, topical betaxolol was added daily. For clarity the average IOPs are not shown, but rats receiving betaxolol had normal IOPs by day 7, while untreated rats had ~1.7-fold increased IOP. Retrogradely labeled surviving RGCs were counted in flat mounted retinas. Statistically reduced RGC death seen in the daily betaxolol group versus the untreated group from day 21 onwards ($p \leq 0.01$). Data reproduced in >3 independent experiments.

| Days | RGC loss (% of normal IOP) | |
|---|---|---|
| post-cautery | Untreated (no betaxolol) | +daily betaxolol (days 4-35) |
| 0 | 0 | 0 |
| 7 | 3 ± 2 | 3 ± 3 |
| 14 | 7 ± 4 | 4 ± 3 |
| 21 | 16 ± 2 | 7 ± 3 |
| 28 | 22 ± 4 | 10 ± 4 |
| 35 | 28 ± 3 | 14 ± 2 |
| 42 | 35 ± 4 | 20 ± 5 |

This reduced rate of RGC loss in eyes whose IOP was normalized with betaxolol was statistically different from untreated eyes ($p \leq 0.005$).

However, the loss of RGCs was reduced, but not prevented, by normalization of IOP. The absolute loss of RGCs in cauterized eyes treated with betaxolol was highly significant at days 35 and 42 compared to normal eyes ($p \leq 0.001$). Thus, complete normalization of pressure shortly after induction of high IOP affords protection to only approximately half of the RGCs that would have died had IOP not been normalized. Chronic RGC loss continues albeit more slowly. Indeed, clinical experience has shown that in spite of successful normalization of IOP, RGC death and subsequent loss of vision often continue in humans also.

function of cholinergic neurons in spatial memory tests. An inactive peptidomimetic with similar structure, termed C59, was used as control.

The experimental paradigm was designed to emulate progression to glaucoma realistically, to treat pre-existing disease and ongoing RGC damage (see experimental flowchart, FIG. 3). Cauterization was performed to induce high IOP for 14 days, a time point at which ~8% RGC loss occurs.

At that point, the TrkA agonist D3, NGF, or controls (i.e., inactive peptidomimetic, saline vehicle) were injected (two independent intraocular injections each of 1 µg compound, at days 14 and 21 after cauterization). These treatments were also combined with or without daily betaxolol treatment (from days 14 to termination at day 42) to normalize IOP. This scenario better reflected the clinical setting in which glaucoma patients are treated with intraocular pressure-lowering drugs.

Surviving RGCs, identified by retrograde labeling, were counted at day 42 post-surgery. In this protocol, the TrkA agonist or controls were not given between days 21 and 42, to evaluate whether any protection could be long-lived. The data are presented in Table 3.

Table 3. Rescue of RGCs in Glaucoma With a TrkA Receptor Agonist.

Each data point represents the average of at least 6 retinas/experimental group±sd. For clarity, the average IOPs are not shown. Peptidomimetic D3 (TrkA agonist) or controls were injected intraocularly, each injection at 1 µg in 1 µl. "—" means no treatment. Ocular pressure was not affected by intraocular injections (glaucoma remains glaucoma, normal remains normal). Retrogradely labeled surviving RGCs at day 42 post-cauterization were counted in flat mounted retinas (except rows 3 and 4 that were terminated at days 14 and 28). Two investigators counted the RGCs, with one unaware of the groups. Similar data was obtained in 3 independent experiments terminated at day 42 and in 1 independent experiment terminated at day 49.

| Row | Eye | Daily Betaxolol | IOP | days of high IOP | Intraocular injections (14 & 21 days) | % RGCs loss at day 42 (vs. Norma |
|---|---|---|---|---|---|---|
| 1 | Normal | — | normal | 0 | — | 0 ± 0 |
| 2 | Normal | — | normal | 0 | Vehicle (PBS) | 4 ± 2 |
| 3 | Cauterized | — | high | 14 | — | 8 ± 5 |
| 4 | Cauterized | — | high | 28 | — | 19 ± 5 |
| 5 | Cauterized | — | high | 42 | — | 36 ± 5 |
| 6 | Cauterized | — | high | 42 | inactive mimetic | 38 ± 6 |
| 7 | Cauterized | — | high | 42 | D3 | 29 ± 3 |
| 8 | Cauterized | days 14 to 42 | high->normal | ~17 | — | 21 ± 2 |
| 9 | Cauterized | days 14 to 42 | high->normal | ~17 | inactive mimetic | 24 ± 4 |
| 10 | Cauterized | days 14 to 42 | high->normal | ~17 | D3 | 11 ± 4 |
| 11 | Cauterized | — | high | 42 | NGF | 42 ± 5 |
| 12 | Cauterized | days 14 to 42 | high->normal | ~17 | NGF | 19 ± 4 |

Example 2

TrkA Receptor Agonist Treatment of Ocular Hypertension

In Vivo RGC Protection With Selective TrkA Agonists

To test TrkA-mediated protection against RGC apoptosis, a small molecule selective TrkA agonist termed D3 was injected intraocularly. D3 was evaluated previously in the CNS, where it was shown to be long-lived and to bind and activate TrkA and to protect the number, phenotype, and Representative pictures of labeled RGCs are shown in FIG. 4.

After 42 days of high IOP, there was a significant loss of 36% RGCs compared to normal IOP eyes (Table 3, row 1 vs. 5; $p \leq 0.001$). RGC loss in high IOP was progressive and time-dependent. There was a loss of 19% RGCs at day 28 high IOP, and 8% RGCs at day 14 high IOP (Table 3, rows 3 and 4). Normalization of IOP with daily application of betaxolol (from day 14 to 42) significantly reduced the loss of RGCs from 36% to 21% (Table 3, row 5 vs. 8; $p \leq 0.005$). However, the 21% RGC loss seen after ~17 days of high IOP and 25 days of normal IOP (endpoint at day 42) was significantly higher than the 8% RGC loss seen after 14 days of high IOP and an endpoint at day 14 (Table 3, row 8 vs. 3; p≤0.005).

Two single intraocular injections of TrkA agonist D3 (at days 14 and 21 of glaucoma) reduced RGC loss on average from 36% to 29% (Table 2, row 7 vs. 5; p≤0.1). This represented protection to ~25% of the RGCs (using the formula $(test_{loss}-day14_{loss})/(day42_{loss}-day14_{loss})*100$), but it was not statistically significant. Treatment with the TrkA agonist D3 in combination with betaxolol significantly reduced RGC loss to 11% (Table 3, row 10). This combination was significantly better than either treatment alone, and represents >90% protection. Indeed, RGC counts in the combination D3+betaxolol were not statistically different than RGC counts in eyes subjected to 14 days of high IOP and an endpoint at day 14 (Table 3, row 10 vs. 3).

In addition, NGF did not protect RGCs from death, whether or not it was combined with betaxolol (Table 3, rows 11 and 12). Control intraocular injections of inactive compounds, or saline, also did not alter RGC counts in normal retinas or in retinas from day 42 glaucoma (Table 3, rows 2 and 6), and did not alter the protective effect of normalizing IOP (Table 3, rows 8 and 9).

It is important to contrast the results in this glaucoma model with those published in optic nerve axotomy (where the optic nerve is sectioned or crushed and RGC axons are damaged). The two are very different models of RGC damage, where glaucoma is chronic and progressive and is an intraocular disease while axotomy is acute and is an extraocular disease. Thus, in optic nerve axotomy NTFs have been applied successfully. The survival of an axotomized optic nerve was promoted by NGF, BDNF, NT-4, CNTF, as well as bFGF, and GDNF. Consistent with these previous studies, the D3 mimetic also showed strong survival-promoting effects on axotomized RGCs.

Example 3 p75 Receptor Antagonist Treatment of Ocular Hypertension

Failure to Protect RGCs in Glaucoma With p75 Receptor Antagonists

The failure of NGF to protect RGCs in glaucoma may be due to activation of pleiotrophic signals, including signals mediated by the p75 receptors themselves. Thus, a similar experimental paradigm was used to study the p75 receptor antagonist C(28-35) to test the potential effect of p75 receptor activation by endogenous neurotrophins (Table 4). The paradigm was altered slightly to an endpoint of 49 days, and the TrkA agonist D3 was included as a positive control.

Table 4. Failure to Rescue RGCs in Glaucoma With a p75 Receptor Antagonist.

Each data point represents the average of 4 retinas/experimental group±sd. For clarity, the average IOPs are not shown. Test peptides and peptidomimetics or controls were injected intraocularly. "—" means no injection. Retrogradely labeled surviving RGCs at day 49 post-cauterization were counted in flat mounted retinas.

| Row | Eye | Daily Betaxolol | IOP | days of high IOP | Intraocular injections (14 & 21 days) | % RGCs loss at day 49 (vs. Normal) |
|---|---|---|---|---|---|---|
| 1 | Normal | — | normal | 0 | — | 0 |
| 2 | Cauterized | — | high | 49 | — | 41 ± 6 |
| 3 | Cauterized | days 14-49 | high->normal | ~17 | — | 27 ± 5 |
| 4 | Cauterized | — | high | 49 | control peptide | 39 ± 5 |
| 5 | Cauterized | days 14-49 | high->normal | ~17 | control peptide | 22 ± 5 |
| 6 | Cauterized | — | high | 49 | D3 | 26 ± 6 |
| 7 | Cauterized | days 14-49 | high->normal | ~17 | D3 | 18 ± 6 |
| 8 | Cauterized | — | high | 49 | C(28-35) peptide | 32 ± 11 |
| 9 | Cauterized | days 14-49 | high->normal | ~17 | C(28-35) peptide | 29 ± 4 |

The p75 receptor antagonist C(28-35) did not enhance RGC survival. After 49 days of high IOP, there was a significant loss of 41% RGCs compared to normal IOP eyes (Table 4, row 1 vs. 2; p≤0.001). Normalization of IOP with daily application of betaxolol (from day 14 to day 49) significantly reduced the loss of RGCs from 41% to 27% (Table 4, row 2 vs. 3; p≤0.01). Further, two single intraocular injections of the p75 receptor antagonist C(28-35) (at days 14 and 21 of glaucoma) did not significantly prevent RGC loss (Table 4, row 8). When C(28-35) was applied alone there was high variability in RGC survival in every experiment, but there was never enhanced protection when C(28-35) was combined with betaxolol treatment (Table 4, row 9), and RGC counts were not different than betaxolol alone (Table 4, row 3). As positive control, treatment with the TrkA agonist D3 (alone or in combination with betaxolol) markedly reduced RGC apoptosis (Table 4, rows 6 and 7); and an irrelevant peptide negative control of C(28-35) had no effect (Table 4, rows 4 and 5).

Overall, the peptide C(28-35) antagonist of p75 did not prevent or reduce RGC death in glaucoma in the time frame of the experiments. However, p75 may be activated by exogenous addition of neurotrophins, and this may explain the failure of NGF to protect RGCs (Table 2). Further, it is possible that there may be detectable protection of RGCs by antagonizing p75 at earlier time-points.

Previous in vivo studies showed that C(28-35) had in vivo stability and efficacy in the CNS. Other studies showed that C(28-35) afforded short-term protection of RGCs in vivo in optic nerve axotomy. Thus, inhibition of p75 receptor activity (e.g., using C(28-35)) may be efficacious in treating ocular hypertension, RGC death and glaucoma, especially in concert with a TrkA receptor agonist.

Example 4

Materials and Methods

Induction of High IOP

All animal procedures were approved by the McGill Animal Welfare Committee. Episcleral cauterization was performed under anesthesia in Wistar rats, female, 8 weeks of age. After a conjunctival incision, extra-ocular muscles were isolated and the major limbal draining veins were identified based on location, relative immobility, larger caliber and branching pattern. Cauterization of three episcleral vessels in the right eye were done with a 30" cautery tip. The left eye in each animal was used as normal IOP control after sham-surgery (conjuctival incisions with no cauterization). There were no IOP differences whether the left or the right eye was cauterized; hence the right side was chosen for record and housekeeping purposes. Planar ophthalmoscopy was used to confirm normal perfusion of the retina at elevated IOP. Cauterization caused an increase of ~1.7-fold in IOP in ~90% of the rats (~10% were discarded and never used experimentally because of extreme high IOP over 1.9-fold, or because they developed cataracts). A 1.7-fold increase is more relevant to human open angle glaucoma than other models that raise pressure >2-fold and often cause ischemia. IOP was measured using a Tonopen XL tonometer under light anesthesia (intramuscular injection of ketamine, 4 mg/kg; xylazine, 0.32 mg/kg; and acepromazine, 0.4 mg/kg). Initially IOP was measured daily (three consecutive readings are taken each time) and then weekly until termination. The accuracy of the readings of the Tonopen compared with other instruments, even under anesthesia, has been established. The mean normal IOP of rats under anesthesia was 12 mm Hg (range 10-14 mm Hg), and in cauterized eyes it was elevated to a stable average 21 mm Hg (range 18-24 mm Hg) for longer than 4 months. These values were consistent with data previously published.

Pharmacological Reduction of High IOP

A selective β-blocker (betaxolol 0.5%, Alcon) was applied daily as eye drops. Topical betaxolol administration was initiated as indicated (e.g. 4 days post-cauterization) resulting in full normalization of IOP after 3 days. IOP continued to remain normalized as long as betaxolol was applied. Betaxolol had no significant effect in the IOP of normal eyes.

Intraocular Injections

A conjunctival incision was made in the superior temporal quadrant of the eye. A puncture was made in the eye wall with a 30 G needle to place a cannula in the orbit. The tip of the needle was inserted at a 45° angle through the sclera into the vitreous body. This route of administration avoided injury to eye structures. A glass cannula (10 μm thickness, prepared with an upright microelectrode puller (Narishige) was connected through plastic tubing to a Hamilton syringe to dispense solutions of test or control substances. Intraocular injections were done at day 14 and 21 post-surgery in sham-operated control eyes with normal IOP, and cauterized eyes with high IOP. The intraocular injections were in 1 μl volumes containing a total of ~1 μg compound. IOP could not be measured immediately after intraocular injections. However, within two days after intraocular injections the high IOP eyes maintained high IOP and the normal IOP eyes maintained normal IOP (data not shown). Thus, chronic ocular pressure appeared to be unaffected by intraocular injections.

Pharmacological Agents

The peptidomimetic D3 is a selective partial agonist of TrkA. D3 binds to and activates TrkA irrespective of whether the p75 receptor is expressed, but it does not bind to p75. The peptide analog of NGF C(28-35) is an antagonist of p75-NGF interactions. C(28-35) has been used in vivo as a p75 receptor antagonist in the CNS in a model of epilepsy.

Retrograde RGC Labeling

RGCs were labeled with 3% DIi (1,1-dioctadecyl-3,3,3,3-tetramethylindocarbocyanine perchlorate) or with 3% Fluorogold. Briefly, rats were anesthetized and their heads were mounted in a stereotactic apparatus. Superior colliculi (SC) were exposed and the dye was injected into each hemisphere at two depths: first at 5.8 mm behind Bregma, 1.0 mm lateral, and depths of 4.5 mm and 3.5 mm.

Flat Mounted Retinas and RGC Counting

Seven days after retrograde labeling, rats were perfused by transcardial administration of phosphate-buffer (PB), followed by 4% PFA in PB and the eyes were immediately enucleated. After post-fixing for 1 hour cuts were made through the sclera and the retinas were detached from the eyecup at the optic nerve head. Retinas were flat-mounted on glass slides (vitreous side up) air-dried and cover-slipped with mounting medium (Molecular Probes). The retinas were observed under fluorescence microscopy (Zeiss). For each retina, four digital images from each quadrant (superior, inferior, nasal and temporal) were taken at 20×. RGCs were recognized in flat mounted retinas by the presence of retrogradely transported dye and by their morphology. Microglia and macrophages, that may have incorporated DiI or FluoroGold after phagocytosis of dying RGCs, were excluded from our analysis of neuronal survival based on their morphology. RGCs counted in all 4 quadrants (16 images per retina) were averaged as the number of RGCs/mm$^2$. For RGC survival, at least 6 eyes for each group were studied (i.e. ±cauterization, ±betaxolol, ±intraocular injections), and experiments were reproduced independently. Samples were coded and RGC counting was done by an experimenter blinded to the code.

The relevant teachings of all references, patents and patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims. All scientific journal articles and patents referred to and/or cited herein, are herein incorporated by reference.

What is claimed is:
1. A method of treating or preventing retinal ganglion cell (RGC) death or glaucoma in a subject comprising administering to the subject an effective amount of:
a) a composition comprising
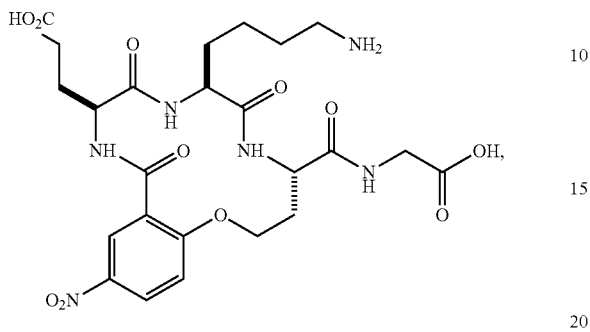
a pharmaceutical carrier; and
b) betaxolol.
2. The method of claim 1 wherein the RGC death is associated with glaucoma.
* * * * *

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Cys Lys Gly Lys Glu Cys
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Cys Asp Ile Lys Gly Lys Glu Cys
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Cys Thr Ala Ile Lys Gly Lys Glu Cys
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Cys Ile Lys Gly Lys Glu Cys
1               5

<210> SEQ ID NO 5
<211> LENGTH: 12
<212> TYPE: PRT
<213> ORGANISM: Artificial Sequence
<220> FEATURE:
<223> OTHER INFORMATION: synthetic peptide

<400> SEQUENCE: 5

Tyr Cys Ala Thr Asp Ile Lys Gly Lys Glu Cys Tyr
1               5                   10